(12) United States Patent
Potgeter et al.

(10) Patent No.: US 8,889,116 B2
(45) Date of Patent: Nov. 18, 2014

(54) ANIMAL ATTRACTANT AND ASSOCIATED DISPENSER

(75) Inventors: Joel D. Potgeter, West Olive, MI (US); Michael A. Rose, Hudsonville, MI (US); David L. Ver Burg, Dorr, MI (US); John E. Bramer, Grandville, MI (US)

(73) Assignee: Deer On A String, Inc., Dorr, MI (US)

( * ) Notice: Subject to any disclaimer, the term of this patent is extended or adjusted under 35 U.S.C. 154(b) by 1258 days.

(21) Appl. No.: 11/801,604

(22) Filed: May 10, 2007

(65) Prior Publication Data

US 2008/0279811 A1   Nov. 13, 2008

(51) Int. Cl.
*A01N 25/34* (2006.01)
*A01N 63/02* (2006.01)
*A01N 65/00* (2009.01)
*A01N 25/18* (2006.01)

(52) U.S. Cl.
CPC ............... *A01N 25/34* (2013.01); *A01N 25/18* (2013.01)
USPC ............ 424/84; 424/405; 424/411; 424/545; 424/777

(58) Field of Classification Search
None
See application file for complete search history.

(56) References Cited

U.S. PATENT DOCUMENTS

| | | | |
|---|---|---|---|
| 4,029,113 A * | 6/1977 | Guyton | .......... 132/321 |
| 5,765,739 A | 6/1998 | Yates, III | |
| 5,806,666 A | 9/1998 | Chiang et al. | |
| 5,947,379 A * | 9/1999 | Freeman | .......... 239/52 |
| 5,996,928 A | 12/1999 | Whitehorse-Burns | |
| 6,295,996 B1 | 10/2001 | Dickie | |
| 6,295,997 B1 | 10/2001 | Dickie | |
| 6,302,121 B1 | 10/2001 | McConnell | |
| 6,488,036 B1 | 12/2002 | Francis | |
| 6,506,395 B2 * | 1/2003 | Lillig | .......... 424/405 |
| 2006/0071092 A1 * | 4/2006 | Harris, Jr. | .......... 239/44 |

OTHER PUBLICATIONS

Deerfarmer.com, The deer urine market (Jul. 25, 2003).*
Bowhunter, Ask Bowhunter (Aug. 1, 2000).*

* cited by examiner

*Primary Examiner* — Abigail Fisher
*Assistant Examiner* — Frank Choi
(74) *Attorney, Agent, or Firm* — King & Partners, PLC

(57) ABSTRACT

A dispenser for an animal attractant including: a housing, wherein the housing includes a chamber for containing a spool; a spool, wherein the spool is associated with the chamber of the housing, and wherein the spool is associated with a deer attractant; and wherein the deer attractant includes a substrate, wherein the substrate is associated with an agent wherein the agent includes a deer attractant.

15 Claims, 2 Drawing Sheets

ANIMAL ATTRACTANT AND ASSOCIATED DISPENSER

CROSS-REFERENCE TO RELATED APPLICATION(S)

Not Applicable

BACKGROUND OF THE INVENTION

1. Field of the Invention

The present invention relates in general to an animal attractant and, more particularly, to an animal attractant that includes a substrate and a deer attracting agent which is preferably associated with a dispenser.

2. Background Art

Hunting animals for both survival and sport has been prevalent in society for centuries. Gun and/or bow hunting for deer is extremely popular in the United States—especially in the Western and Midwestern states. One of the more popular deer hunting tactics is to lure a deer within a reasonable shooting distance with bates and/or attractants.

Common bates and/or attractants include foods that are consumed by deer, as well as various forms of deer urine. While utilization of deer urine has become increasingly popular among deer hunters, storing, dispensing, and/or utilizing this particular attractant remains largely problematic.

For example, deer urine is typically provided in liquid form which must be retained in a bottle or container, which can be problematic with respect to storage and/or spillage during normal field use.

With regard to dispensing/utilizing deer urine, hunters will typically spray the urine near a desired location. However, wind and other climate conditions can render dispensing the deer urine problematic if not futile—especially in gusty conditions where the hunter may get dosed with urine from wind shear. For many hunters, getting dosed with deer urine can substantially diminish the satisfaction of the overall hunting experience—especially for those hunters who are susceptible to headaches from the pungent aroma of urea based liquids.

Accordingly, it is an object of the present invention, among others, to provide an animal attractant and associated dispenser which overcomes the aforementioned problems associated with storing, dispensing, and/or utilizing, for example, deer urine.

These and other objects of the present invention will become apparent in light of the present specification, claims, and drawings.

SUMMARY OF THE INVENTION

In one embodiment, the present invention is directed to a deer attractant, comprising: (a) a substrate, wherein the substrate is associated with an agent; and (b) wherein the agent comprises a deer attractant.

In a preferred embodiment of the present invention, the substrate is impregnated (e.g. infused, soaked, steeped, saturated, drenched, permeated, pervaded, suffused, imbued, etcetera) with the agent.

In another preferred embodiment of the present invention, the substrate comprises at least one of natural and synthetic fibers. Natural fibers may include cotton, wool, linen, jute, flax, ramie, sisal, hemp, and mixtures thereof—just to name a few. Synthetic fibers may include rayon, nylon, polyester, saran, spandex, vinalon, nomex, kevlar, twaron, lyocell, zylon, vectran, and mixtures thereof—among many other fibers.

In yet another preferred embodiment of the present invention, the substrate comprises floss, such as, but not limited to, those utilized in dental and/or medical applications. In this embodiment the floss may be fabricated from silk, nylon, and polytetrafluoroethylene, and combinations thereof—as well as numerous other materials.

In another aspect of the present invention, the agent or deer attractant preferably comprises natural and/or synthetic deer urine, and may include, among others, doe urine, doe urine in estrous, and/or buck urine.

In another aspect of the present invention, the agent and/or the substrate may be augmented with a secondary deer attractant such as human urine and/or extracts of fruit.

In yet another aspect of the present invention, at least a portion of the floss is at least partially covered with a wax.

In one embodiment, the present invention is also directed to a dispenser for a deer attractant, comprising: (a) a housing, wherein the housing includes a chamber for containing a spool; (b) a spool, wherein the spool is associated with the chamber of the housing; and (c) a deer attractant as disclosed herein, wherein the deer attractant is associated with the spool.

BRIEF DESCRIPTION OF THE DRAWINGS

The invention will now be described with reference to the drawings wherein.

DETAILED DESCRIPTION OF THE INVENTION

Figure 1:
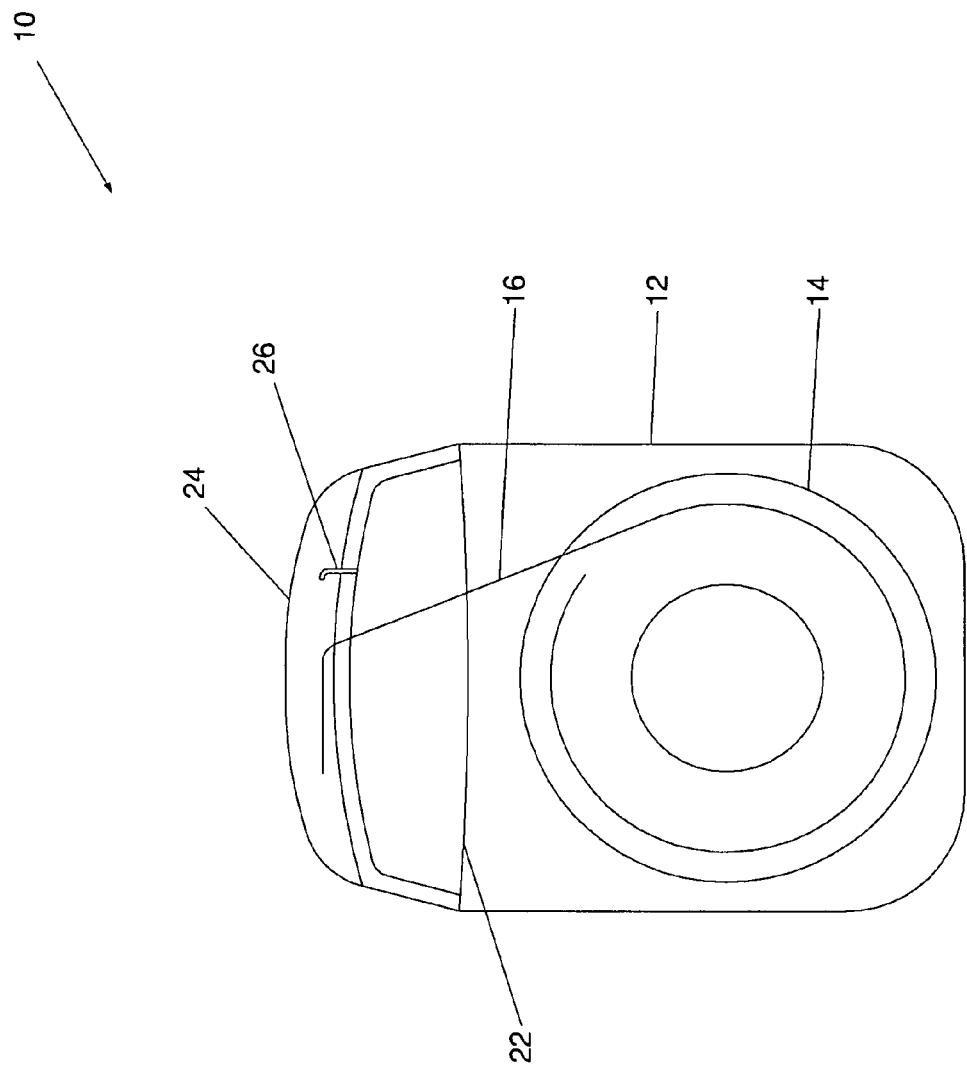
FIG. 1 is a perspective representation of a deer attractant dispenser fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Figure 2:
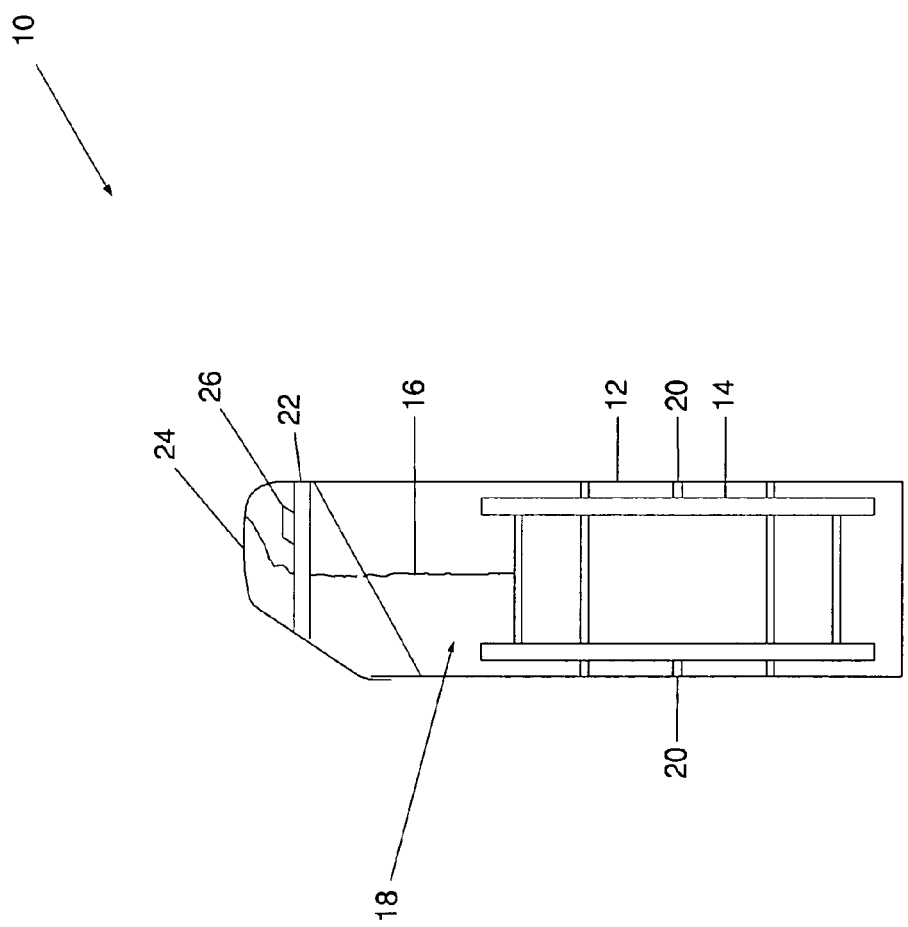
FIG. 2 is a cross-sectional representation of a deer attractant dispenser fabricated in accordance with the present invention.

Referring now to the drawings and to FIGS. 1 and 2 collectively, animal attractant dispenser 10 is shown, which generally comprises housing 12, spool 14, and deer attractant 16. As will be explained in greater detail below, it will be understood that, during normal use of animal dispenser 10, a hunter can store and dispense an attractant (i.e. lure and/or bait) without the drawbacks disclosed supra. It will be understood that the above-identified Figures are merely schematic representations of animal dispenser 10. As such, some of the components may have been distorted from their actual scale for pictorial clarity.

Housing 12 of animal attractant dispenser 10 preferably includes chamber 18 for containing spool 14. Housing 12 is preferably at least substantially sealed to prevent any odor from emanating therefrom. While housing 12 has been disclosed in an embodiment herein, it will be understood that housing 12 may be configured in a analogous manner to any one of a number of dental floss type dispensers, including those disclosed in U.S. Pat. Nos. 5,765,739, 5,806,666, 5,996,928, 6,295,996, 6,295,997, 6,302,121, and 6,488,036—all of which are hereby incorporated herein by reference in their entirety including the references cited therein. Housing 12 is preferably fabricated from a natural and/or synthetic plastic resin. However any one of a number of materials that would be known to those having ordinary skill in the art with the present disclosure before them are likewise contemplated for use.

Spool 14 of animal attractant dispenser 10 is associated with chamber 18. As will be discussed in greater detail below, spool 14 is associated with a deer attractant and serves to releasably retain the same in a generally reeled configuration. Spool 14 is preferably secured to housing 12 in such a manner that it is substantially free to rotate upon dispensing of a deer attractant. In one embodiment spool 14 includes tabs 20 which are received in mating slots of housing 12. It will be understood that a reciprocal configured is likewise contemplated for use in accordance with the present invention wherein spool 14 includes slots for receiving tabs associated with housing 12.

In one embodiment of the present invention, animal attractant dispenser 10 includes living hinge 22 which enables top 24 of dispenser 10 to be manipulated to and/or from an open and/or closed position while being fixedly attached to dispenser 10 along at least one seem. It will be understood that when top 24 is in a closed position, animal attractant dispenser 10 is preferably substantially sealed in such a manner that odors are substantially precluded from emanating therefrom.

In another embodiment of the present invention, animal attractant dispenser 10 includes knife 26 which enables a substrate of deer attractant 16 to be rapidly cut to any desired length. It will be understood that regardless of its ordinary meaning the term "knife" includes any member and/or object which is capable of cutting the substrate of deer attractant 16 to any desired length.

Deer attractant 16 of animal attractant dispenser 10 is preferably associated with spool 14, and comprises a substrate, wherein the substrate is associated with an agent, wherein the agent comprises a deer attractant.

In a preferred embodiment of the present invention, the substrate is impregnated (e.g. infused, soaked, steeped, saturated, drenched, permeated, pervaded, suffused, imbued, etcetera) with the agent.

In one aspect of the present invention, the substrate may comprise natural and/or synthetic fibers. Non-limiting examples of natural fibers include, cotton, wool, linen, jute, flax, ramie, sisal, hemp, and mixtures thereof—just to name a few. Non-limiting examples of synthetic fibers include rayon, nylon, polyester, saran, vinalon, nomex, kevlar, twaron, lyocell, zylon, vectran, and mixtures thereof.

In another embodiment of the present invention, the substrate comprises floss. The floss may be fabricated from, for example, silk, nylon, and polytetrafluoroethylene, and combinations thereof.

In accordance with the present invention the agent preferably includes natural deer urine and/or synthetic deer urine, including, but not limited to, doe urine, doe urine in estrous, and/or buck urine.

An augmentant may also be associated with (e.g. impregnated) the substrate, such as, but not limited to, human urine, extracts of fruit, etcetera.

In another aspect of the present invention, at least a portion of the substrate may be at least partially covered with a wax. Such a coating can control the intensity of an associated odor, as well as preserve the integrity of the odor and/or substrate.

In operation, a user can rapidly dispense the deer attractant while in the field without concern regarding spilling and/or spraying the attractant. In addition, the attractant can be quickly attached and/or secured to tree branches, bushes, etcetera, and rapidly removed—if desired. Indeed, such an attractant alleviates the problems associated with conventional attractants as disclosed herein.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A dispenser for a deer attractant, comprising:
   a housing, wherein the housing includes a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;
   a living hinge formed between the top wall and the back wall;
   a knife adapted to cut a substrate, wherein the knife is positioned proximate the top wall of the housing;
   a spool, wherein the spool includes a first spool tab and a second spool tab, wherein the first spool tab is releasably inserted into the first slot of the front wall and the second spool tab is releasably inserted into the second slot of the back wall; and
   a substrate, wherein the substrate is positioned around the spool and wherein the substrate is associated with an agent,
   wherein the agent comprises a deer attractant.

2. The dispenser according to claim 1, wherein the substrate is impregnated with the deer attractant.

3. The dispenser according to claim 2, wherein the substrate comprises at least one of natural and synthetic fibers.

4. The dispenser according to claim 3, wherein the substrate comprises natural fibers selected from the group consisting of cotton, wool, linen, jute, flax, ramie, sisal, hemp, and mixtures thereof.

5. The dispenser according to claim 3, wherein the substrate comprises synthetic fibers selected from the group consisting of rayon, nylon, polyester, saran, spandex, vinalon, nomex, kevlar, twaron, lyocell, zylon, vectran, and mixtures thereof.

6. The dispenser according to claim 3, wherein the substrate consists of floss.

7. The dispenser according to claim 6, wherein the floss consists of a material selected from the group consisting of silk, nylon, polytetrafluoroethylene, and combinations thereof.

8. The dispenser according to claim 6, wherein at least a portion of the floss is at least partially covered with a wax.

9. The dispenser according to claim 6, wherein at least a portion of the floss is covered with a wax.

10. The dispenser according to claim 3, wherein the agent comprises natural deer urine.

11. The dispenser according to claim 3, wherein the agent comprises synthetic deer urine.

12. The dispenser according to claim 3, wherein the agent comprises at least one of doe urine, doe urine in estrous, and buck urine.

13. The dispenser according to claim 12, wherein the agent further comprises an augmentant comprising at least one of human urine and extracts of fruit.

14. A dispenser for a deer attractant, comprising:

a housing, wherein the housing includes a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;

a living hinge formed between the top wall and the back wall;

a knife adapted to cut a substrate, wherein the knife is positioned proximate the top wall of the housing;

a spool, wherein the spool includes a first spool tab and a second spool tab, wherein the first spool tab is releasably inserted into the first slot of the front wall and the second spool tab is releasably inserted into the second slot of the back wall; and a substrate consisting of floss, wherein the substrate is positioned around the spool and wherein the substrate is associated with an agent, wherein the agent comprises natural and/or synthetic deer urine and extracts of fruit, and wherein at least a portion of the floss is at least partially covered with a wax.

15. A dispenser for a deer attractant, consisting of:

a housing, wherein the housing consists of a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;

a living hinge formed between the top wall and the back wall;

a knife adapted to cut a substrate, wherein the knife is positioned proximate the top wall of the housing;

a spool, wherein the spool includes a first spool tab and a second spool tab, wherein the first spool tab is releasably inserted into the first slot of the front wall and the second spool tab is releasably inserted into the second slot of the back wall; and a substrate consisting of floss, wherein the substrate is positioned around the spool and wherein the substrate is associated with an agent, wherein the agent consists of natural and/or synthetic deer urine, and wherein at least a portion of the floss is at least partially covered with a wax.

\* \* \* \* \*